United States Patent [19]

Hemmerle et al.

[11] Patent Number: 5,739,147

[45] Date of Patent: Apr. 14, 1998

[54] CYCLOHEXANE DERIVATIVES, PROCESS FOR THEIR PREPARATION, AND THE USE OF THE COMPOUNDS FOR THE TREATMENT OF DISEASES

[75] Inventors: Horst Hemmerle, Lorsch; Gerrit Schubert, Kelkheim; Hans-Jörg Burger, Frankfurt; Andreas Herling, Bad Camberg; Suad Efendic', Lidingö, all of Germany

[73] Assignee: Hoechst Aktiengesellschaft, Frankfurt am Main, Germany

[21] Appl. No.: 861,120

[22] Filed: May 21, 1997

Related U.S. Application Data

[63] Continuation of Ser. No. 433,859, May 2, 1995, abandoned.

[30] Foreign Application Priority Data

May 10, 1994 [DE] Germany .................. 44 16 433.5

[51] Int. Cl.$^6$ .................. A61K 31/44; C07D 471/04
[52] U.S. Cl. .................. 514/303; 546/118
[58] Field of Search .................. 546/118; 514/303

[56] References Cited

U.S. PATENT DOCUMENTS 5,463,062  10/1995  Hemmerle .................. 546/168

FOREIGN PATENT DOCUMENTS 0587087  3/1994  European Pat. Off.
0587088  3/1994  European Pat. Off.

*Primary Examiner*—C. Warren Ivy
*Assistant Examiner*—Evelyn Huang
*Attorney, Agent, or Firm*—Finnegan, Henderson, Farabow, Garrett & Dunner, L.L.P.

[57] ABSTRACT

Cyclohexane derivatives, process for their preparation, and the use of the compounds for the treatment of diseases Cyclohexane derivatives of the formula I

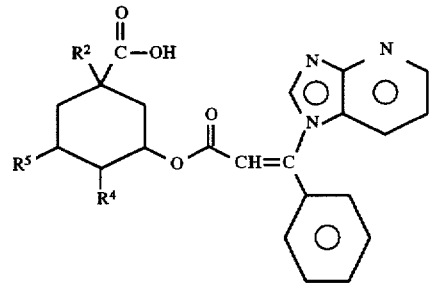

wherein $R^2$, $R^4$ and $R^5$ have the given meanings and a process for their preparation are described. The compounds have useful pharmacological properties and can therefore be used as pharmaceuticals.

13 Claims, No Drawings

CYCLOHEXANE DERIVATIVES, PROCESS FOR THEIR PREPARATION, AND THE USE OF THE COMPOUNDS FOR THE TREATMENT OF DISEASES

CROSS-REFERENCE TO RELATED APPLICATION

This is a continuation of application Ser. No. 08/433,859, filed May 2, 1995, abandoned which is herein incorporated by reference.

DESCRIPTION

Cyclohexane derivatives, process for their preparation, and the use of the compounds for the treatment of diseases EP-A-0 587 088 relates to substituted cyclohexane derivatives of the formula A

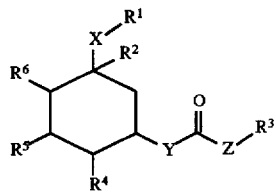

which inhibit the glucose-6-phosphatase system of the liver in mammals and can therefore be used as pharmaceuticals.

In formula A, the various radicals have the following meanings:

$R^1$: CN, COOH, a COOH group protected by a protective group, $C_1$–$C_4$-alkanoyl, $SO_3$—$C_1$–$C_4$-alkyl, $SO_3H$, $SO_2NR^8R^9$, $PO(OH)_2$, $PO(OH)(O$—$C_1$–$C_4$-alkyl), $PO(O$—$C_1$–$C_4$-alkyl)$_2$, $R^2$: $C_1$–$C_{10}$-alkyl $(R^{11})_n$, $O$—$C_1$–$C_{10}$-alkyl $(R^{11})_n$, $C_2$–$C_{10}$-alkenyl $(R^{11})_n$, $O$—$C_3$–$C_{10}$-alkenyl $(R^{11})_n$, $C_2$–$C_{10}$-alkynyl $(R^{11})_n$, $O$—$C_3$–$C_{10}$-alkynyl $(R^{11})_n$, $S$—$C_1$–$C_{10}$-alkyl $(R^{11})_n$, $S$—$C_3$–$C_{10}$-alkenyl $(R^{11})_n$, $S$—$C_3$–$C_{10}$-alkynyl $(R^{11})_n$, $NH$—$C_1$–$C_{10}$-alkyl $(R^{11})_n$, $NH$—$C_3$–$C_{10}$-alkenyl $(R^{11})_n$ or $NH$—$C_3$–$C_{10}$-alkynyl $(R^{11})_n$, where $R^{11}$ is optionally substituted in each case by $R^{12}$;

$R^3$, $R^{11}$ and $R^{13}$: alkyl having 1 to 10 carbon atoms, cycloalkyl having 3–8 ring carbon atoms, phenyl, naphthyl, phenanthryl, pyridyl, thienyl, furyl, pyrimidyl, indolyl, imidazolyl, coumarinyl, phthaliminyl, quinolyl, piperazinyl, tetrazolyl, triazolyl, oxazolyl, or their thieno, pyridino, pyrimidino or benzo-fused derivatives, where the aromatic or heteroaromatic can be substituted one or more times in an identical or different manner by F, Cl, Br, I, OH, $CF_3$, —$NO_2$, CN, $C_1$–$C_4$-alkoxy, $C_1$–$C_4$-alkyl, $NR^8R^9$, phenyl, benzyl, thienyl, furyl, imidazolyl, pyridyl, O-phenyl or O-benzyl substituents, and $R^3$, $R^{11}$ and $R^{13}$ are identical or different;

$R^4$, $R^5$ and $R^6$: H, OH, an OH group protected by customary alcohol protective groups, F, Cl, Br, or have the meanings given for $R^2$, where $R^4$, $R^5$ and $R^6$ are identical or different;

$R^7$: $C_1$–$C_4$-alkyl, phenyl or benzyl;

$R^8$ and $R^9$: H, $C_1$–$C_4$-alkyl, $C_1$–$C_4$-alkanoyl, phenyl which is optionally substituted by F, Cl, Br, I, OH, $O$—$C_1$–$C_4$-alkyl, $CF_3$, —$NO_2$ or CN, where $R^8$ and $R^9$ are identical or different, or $R^8$ and $R^9$, together with the nitrogen atom, form a 4- to 10-membered, saturated heterocyclic ring in which one $CH_2$ group can optionally be replaced by O, S or $NR^{10}$, $R^{10}$: H, $C_1$–$C_4$-alkyl, phenyl or benzyl $R^{12}$: phenyl, naphthyl, phenanthryl, pyridyl, thienyl, furyl, pyrimidyl, indolyl, imidazolyl, coumarinyl, phthaliminyl, quinolyl, piperazinyl, tetrazolyl, triazolyl, oxazolyl, or their thieno or benzo-fused derivatives, where the aromatic or heteroaromatic can be substituted one or more times in an identical or different manner by F, Cl, Br, I, OH, $CF_3$, —$NO_2$, CN, $C_1$–$C_4$-alkoxy, $C_1$–$C_4$-alkyl, $C_2$–$C_4$-alkenyl, $NR^8R^9$, phenyl, benzyl, thienyl, furyl, imidazolyl, pyridyl, O-phenyl or O-benzyl substituents;

X: $(CH_2)_m$, —CH=CH—, —C≡C—, —$CH_2$—O—$CH_2$—, —$CH_2$—S—$CH_2$— or $$-CH_2-\underset{R^8}{N}-CH_2-,$$

Y: $(CH_2)_m$, O, S, $NR^8$,

Z: $(CH_2)_m$, S, O, S—$C_1$–$C_{10}$-alkyl, O—$C_1$–$C_{10}$-alkyl, CH=CH, CH=CF, CH=CCl, CH=CBr, $CH_2$—CO, $CH_2$—CHF, $CH_2$—CHCl, $CH_2$—CHBr, $CH_2$—CHI, $C_3$–$C_{10}$-cycloalkylene, $C_3$–$C_{10}$-cycloalkenylene, where 1 to 3 ring carbon atoms can be replaced by sulfur, oxygen or nitrogen atoms, $COOR^7$, C≡C, CH=C($C_1$–$C_4$-alkyl), CH=C(CN), CH=C($NR^8R^9$), CH=C($C_1$–$C_4$-alkanoyl), CH=C($R^{13}$), $NR^8$ and, if Y is oxygen, $$-\underset{O}{\overset{\|}{C}}-Z-R^3$$

together can be an amino acid radical selected from the group consisting of Ala, Arg, Asn, Asp, Cys, Gln, Glu, Gly, His, Ile, Leu, Lys, Phe, Pro, Set, Thr, Trp, Tyr and their derivatives protected by customary protective groups, n: zero, 1 or 2, m: zero, 1, 2, 3 or 4.

It was then completely surprisingly found that compounds of the formula A which carry very special radicals and are not described in EP-A-0 587 088 have an extremely strong inhibitory action on the glucose-6-phosphatase system of the liver in mammals.

The invention therefore relates to cyclohexane derivatives of the formula

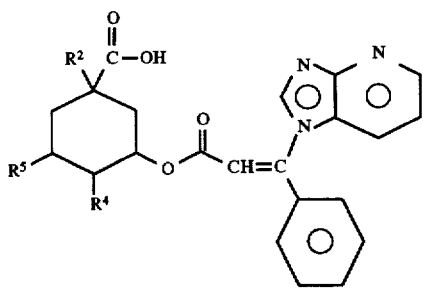

wherein

R² is O—C₃–C₅-alkyl (R¹¹), where the alkyl moiety is straight-chain, branched or cyclic and R¹¹ is phenyl which is optionally substituted in the 4-position by fluorine, chlorine or methyl, and R⁴ and R⁵ are identical or different and/or are OH, and their physiologically tolerable salts.

The compounds of the formula I according to the invention contain a number of stereocenters. The invention relates to all possible enantiomers and diastereomers. They are all represented by the formula I.

The action of the compounds according to the invention on the glucose-6-phosphatase system was investigated in an enzyme assay in liver microsomes.

Fresh liver organs of male Wistar rats were used for the preparation of the microsome fraction containing the glucose-6-phosphatase and worked up as described in the literature [Canfield, W. K. and Arion, W. J., J. Biol. Chem. 263, 7458–7460, (1988)]. This microsome fraction can be stored at –70° C. for at least 2 months without significant loss of activity.

The detection of the glucose-6-phosphatase activity was carried out as given in the literature (Arion, W. J. in Methods Enzymol. 174, Academic Press 1989, pages 58–67) by determination of the phosphate released from glucose-6-phosphate. 0.1 ml of test mixture contained glucose-6-phosphate (1 mmol/l), the test substance, 0.1 mg of microsome fraction and 100 mmol/l of HEPES buffer (4-(2-hydroxyethyl)piperazine-1-ethanesulfonic acid), pH 7.0. The reaction was started by addition of the enzyme. After the passage of 20 min at room temperature, the reaction was stopped by addition of 0.2 ml of phosphate reagent. The sample was incubated at 37° C. for 30 min, and the absorption (A) of the blue color was then measured at 570 nm. The inhibitory activity of the test substance resulted by comparison with a control reaction which contained no test substance, according to the formula $$\text{Percentage inhibition} = \frac{A(\text{control}) - A(\text{test substance})}{A(\text{control})} \times 100$$

If necessary, the inhibitory action of the test substance was determined as a function of the concentration of the test substance employed, and the concentration for the 50% inhibition of the enzyme activity ($IC_{50}$) calculated from this.

The $IC_{50}$ value was determined for the compounds shown below:

EXAMPLE 1

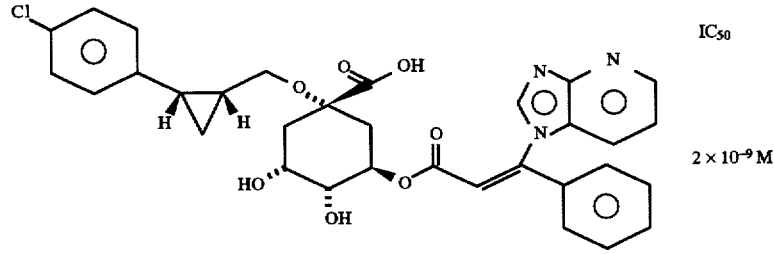

$IC_{50}$ $2 \times 10^{-9}$ M

EXAMPLE 2

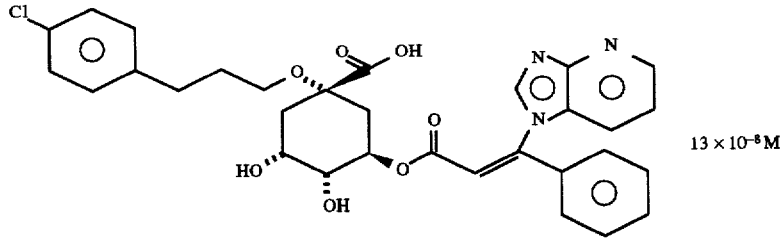

$13 \times 10^{-8}$ M

EXAMPLE 3
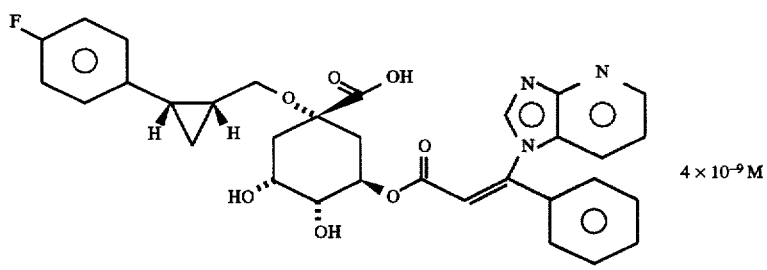
$4 \times 10^{-9} M$
EXAMPLE 4
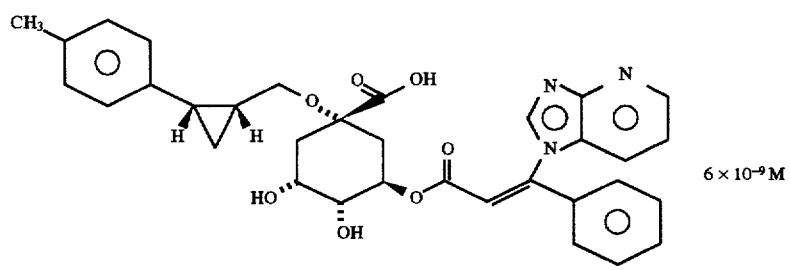
$6 \times 10^{-9} M$
EXAMPLE 5
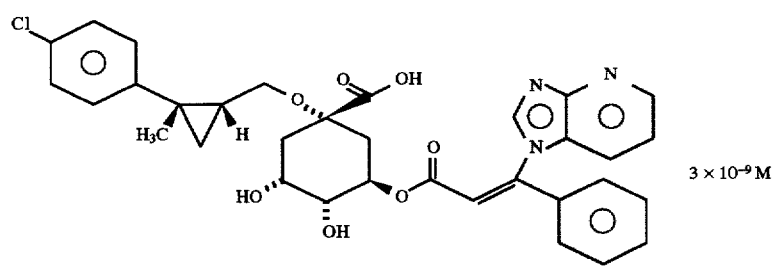
$3 \times 10^{-9} M$
EXAMPLE 6
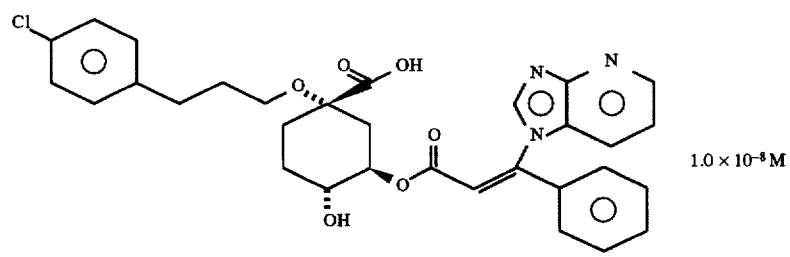
$1.0 \times 10^{-8} M$

EXAMPLE 7

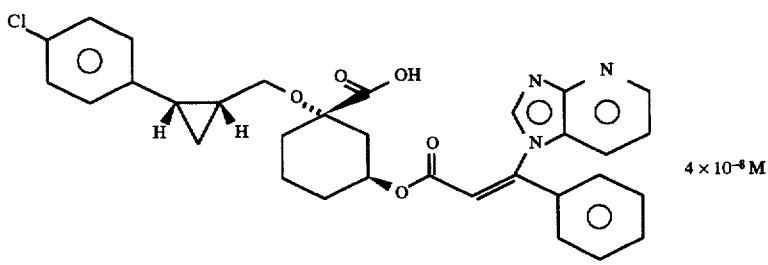

4 × 10⁻⁸ M

The compounds according to the invention are thus a selection compound from the compounds claimed in EP-A-0 587 088.

The compounds of the formula I according to the invention are prepared analogously to the process described in EP-A-0 587 088, if $R^2$=O—$C_3$-$C_5$-cycloalkyl ($R^{11}$) the reaction being advantageously carried out analogously to the process for the preparation of the starting material proposed in German Patent Application P 44 13 402.9.

EXAMPLE 1
1. Preparation of the starting compound 1e
Stage a:

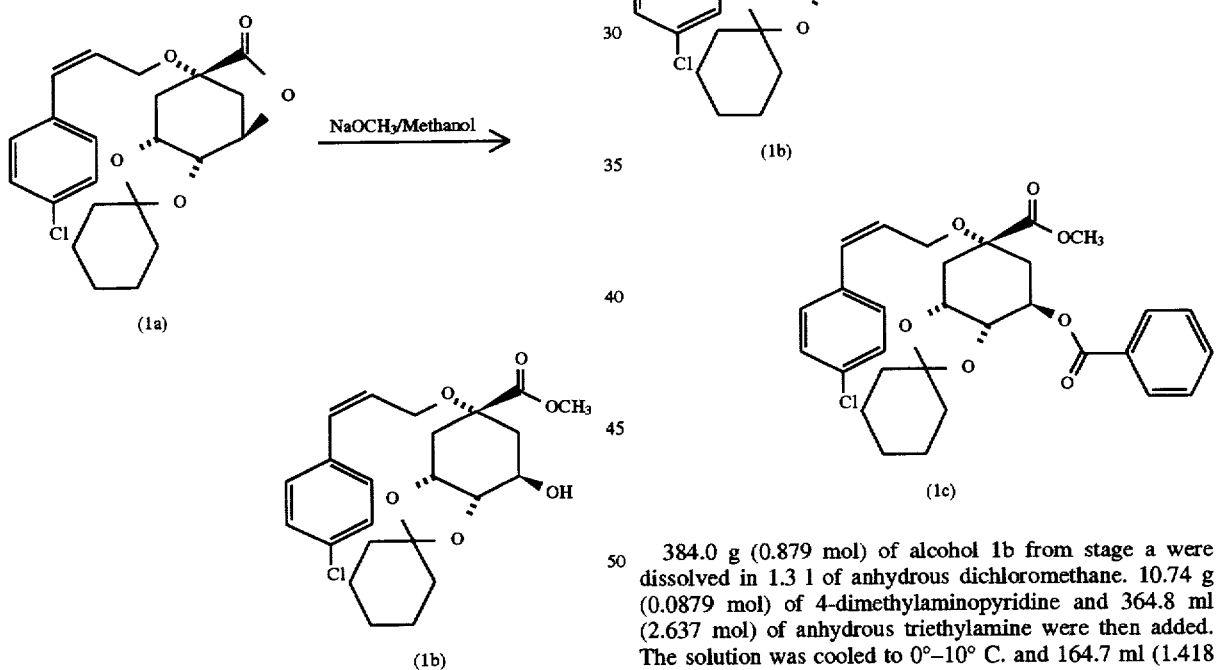

2.95 g (0.0985 mol) of NaH, 80% strength, were added in portions at room temperature under an argon atmosphere to a solution of 5 l of anhydrous methanol and 1.5 l of anhydrous tetrahydrofuran. Compound 1 (cf. EP-A-0 587 088) was then added as a solid, likewise at room temperature. After 3–4 hours a clear solution was obtained. For working up, 6.0 g of glacial acetic acid (pH~5) and then, in portions, 2 l of water were added. A flocculent precipitate of unreacted lactone was formed, which could be filtered off without problems. (Recovery of starting material!)

The filtrate was then concentrated until a thick white precipitate was formed. The mixture was cooled with ice, and the precipitate was filtered off with suction and washed with ice-cold methanol/water 1:1.

After drying the precipitate at 1 mbar and 40° C., 370 g (86%) of compound 1b were obtained as a colorless solid.
M.p.: 102°–104° C.
Stage b:

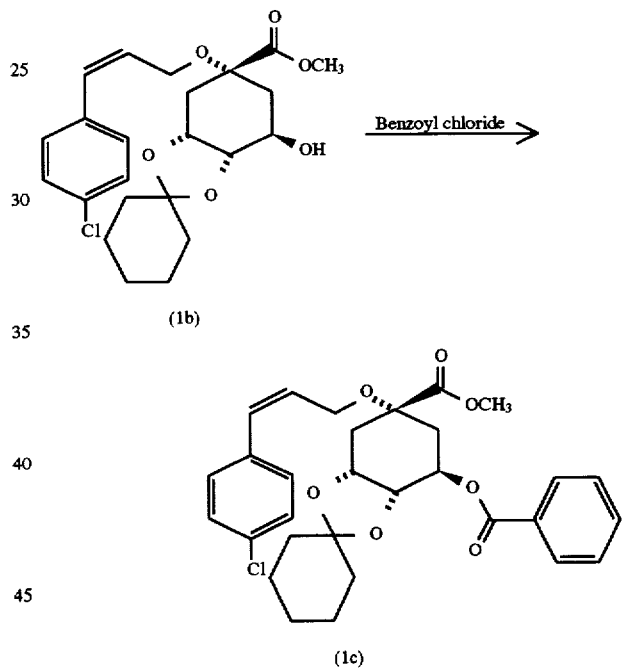

384.0 g (0.879 mol) of alcohol 1b from stage a were dissolved in 1.3 l of anhydrous dichloromethane. 10.74 g (0.0879 mol) of 4-dimethylaminopyridine and 364.8 ml (2.637 mol) of anhydrous triethylamine were then added. The solution was cooled to 0°–10° C. and 164.7 ml (1.418 mol) of benzoyl chloride dissolved in 350 ml of anhydrous dichloromethane were then added dropwise. After 4 hours at room temperature only traces of starting material were present.

TLC: ethyl acetate/cyclohexane 1:2

The reaction product was added to 1.5 l of water/400 g of NH₄Cl/1 l of ice. It was then extracted twice with dichloromethane, and the combined organic phases were washed once with saturated bicarbonate solution and dried using $Na_2SO_4$. After concentrating, the residue was crystallized from isopropanol.

437.0 g (91.9%) of product 1c were obtained.
M.p.: 104°–107° C.

Stage c:

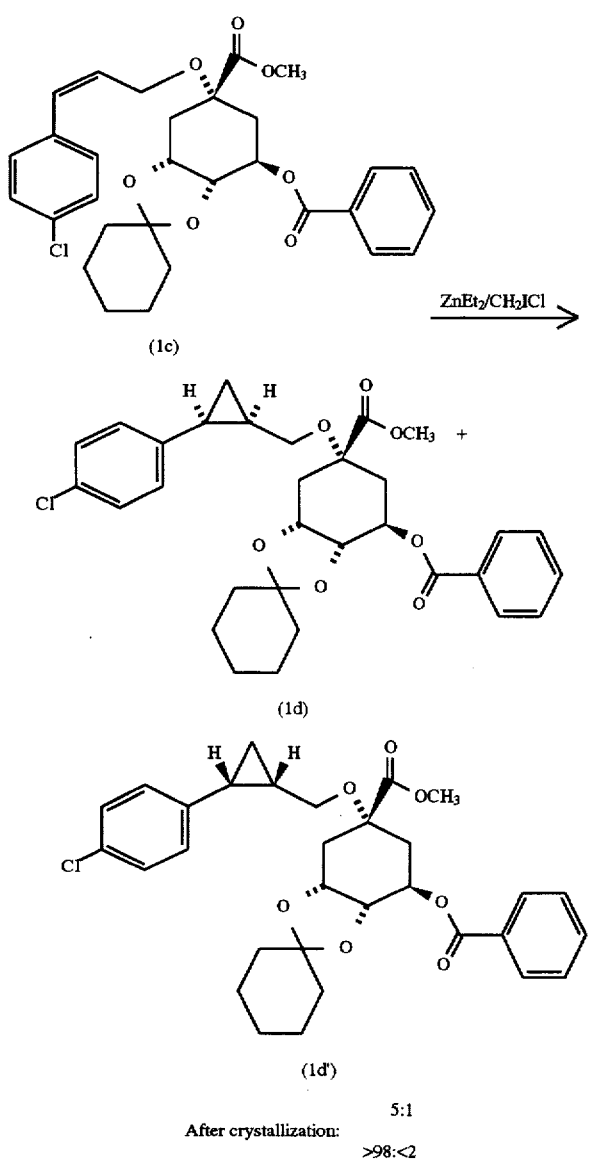

After crystallization: 5:1
>98:<2

80.5 ml (0.785 mol) of pure diethylzinc* were transferred under pressure from a steel cylinder at 0° C. under an argon atmosphere to 2 l of anhydrous dichloroethane** with the aid of a steel cannula.

* instead of pure diethyl zinc a 1 molar solution in toluene (Aldrich) can also be used.
** instead of dichloroethane other inert solvents were also used (dichloromethane, toluene, THF).

114.4 ml (1.57 mol) of chloroiodomethane were then added dropwise at 0°–10° C., the resulting suspension was stirred for 30 minutes and after that 169.89 g (0.314 mol) of the olefin 1c from stage b, dissolved in 500 ml of anhydrous dichloroethane, were added dropwise. After 1 hour at 0°–10° C., the reaction mixture was allowed to warm to room temperature and stirred at room temperature for a further 3 hours.

The reaction mixture was poured slowly under a nitrogen atmosphere into a solution of 300 g of NH$_4$Cl/1.5 l of ice water and extracted with dichloromethane. The combined organic phases were extracted by shaking with saturated NaCl solution and dried using Na$_2$SO$_4$.

Most of the solvent was then evaporated in vacuo and the residue was diluted with isopropanol. The mixture was then concentrated further until a thick precipitate was deposited. This precipitate was filtered off with suction and recrystallized twice from isopropanol, and 109.8 g (63%) of compound 1d having a DE>98% were obtained.

M.p.: 143°–144° C.

* instead of pure diethyl zinc a 1 molar solution in toluene (Aldrich) can also be used.
** instead of dichloroethane other inert solvents were also used (dichloromethane, toluene, THF).

Stage d:

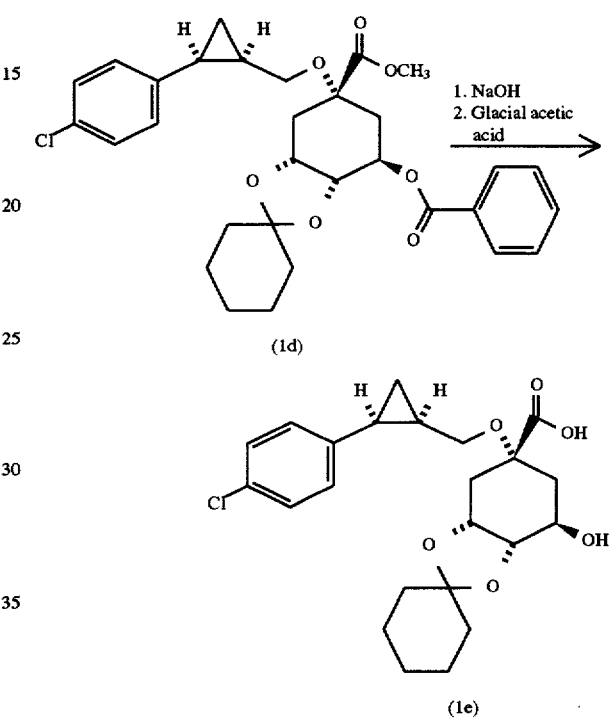

99.0 g (0.178 mol) of compound 1d from stage c were dissolved in 1200 ml of dioxane and 890 ml of 2N sodium hydroxide solution were added. The suspension was warmed at 80° C. for 2 hours.

The reaction solution was cooled down to about 10° C. and 228 ml (2 mol) of half-conc. glacial acetic acid were slowly added dropwise (pH 5–6). The solution was then concentrated on a rotary evaporator until the first turbidity occurred. This concentrate was poured with vigorous stirring onto about 1500 ml of water, from which, after stirring for 10 minutes, a crystalline precipitate was deposited. This precipitate was filtered off with suction and dried in vacuo at 22° C. and 0.5 bar. 82.2 g of compound 1e were obtained.

2. Preparation of the starting compound of the formula 1F

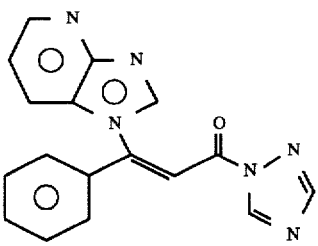

is carried out analogously to the details in EP-A-0 587 088 according to the following reaction scheme:

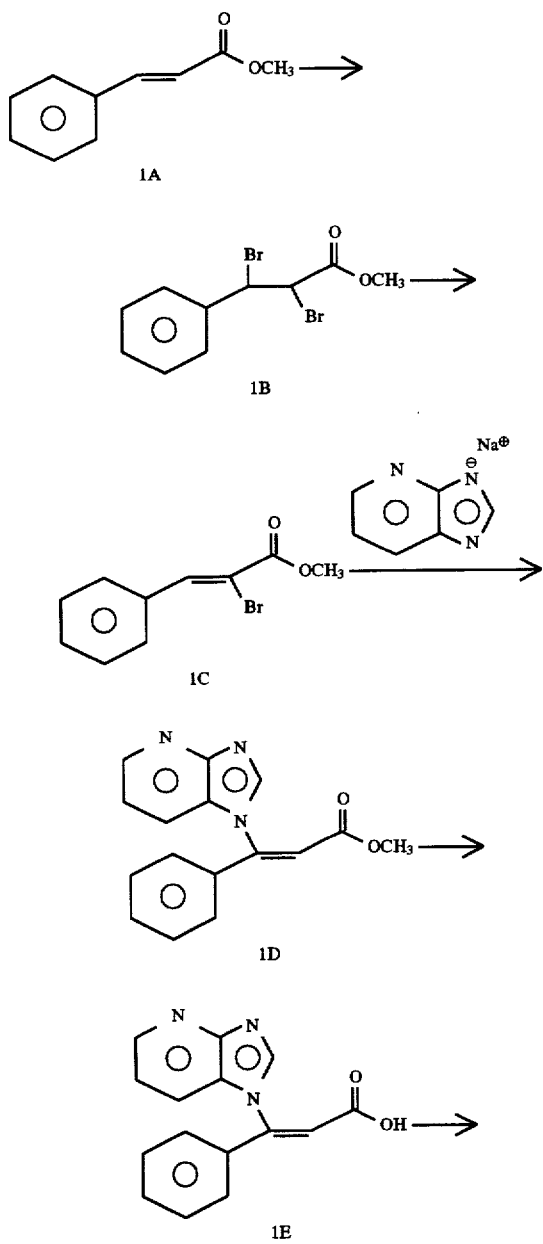

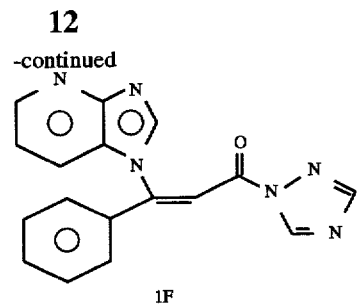

Preparation of 1B from 1A:

162 g (1 mol) of 1A are dissolved in 400 ml of dichloromethane. 31.4 ml of bromine are added dropwise at 0°–15° C. The mixture is stirred at 15° C. for 2 h and concentrated in vacuo. 261 g of 1B are obtained as a colorless solid.

Preparation of 1D from 1B:

A mixture of 50 g of methyl 2,3-dibromo-3-phenylpropanoate 1B, 100 ml of triethylamine and 500 ml of toluene is heated to boiling for 1 h, then cooled to room temperature and filtered. The filtrate is evaporated in vacuo and the α-bromocinnamic acid 1C thus obtained is reused without purification. 0.2 mol of imidazopyridine, dissolved in 150 ml of anhydrous DMF, is added dropwise with stirring to a suspension of 4.7 g of NaH (80% strength in mineral oil) in 100 ml of anhydrous DMF. During this process, the temperature of the mixture is kept below 35° C. by cooling with ice. After addition is complete, the mixture is stirred at room temperature for 1 h. The α-bromocinnamic acid previously prepared is dissolved in 200 ml of anhydrous DMF and the solution of the azole sodium salt is added dropwise with stirring while cooling with ice. After stirring at room temperature for 2 hours, 10.8 ml of glacial acetic acid are added, the mixture is stirred into 1.5 l of ice water and extracted several times with ethyl acetate, and the organic phases are washed with water. The organic phases are dried and evaporated in vacuo, and the residue is crystallized from ethyl acetate. 37.0 g of 1D are obtained as pale yellow crystals.

Preparation of 1E from 1D:

27.0 g (0.097 mol) of 1D were dissolved in 200 ml of methanol. 100 ml of 2.5N NaOH were added. This solution is stirred at 22° C. for 12 h. 200 ml of 2N acetic acid are then added dropwise. The precipitate which was deposited was filtered off with suction and washed with ethyl acetate. 22.0 g of 1E are obtained as a colorless solid.

Preparation of 1F from 1E:

9.2 g (34.7 mmol) of 1E were dissolved in 170 ml of dimethylformamide and 6.5 g (38.2 mmol) of carbonylditriazole were added at 22° C. The suspension was heated at 50°–60° C. for 1 hour and a clear yellow solution of 1F in dimethylformamide was obtained, which was employed in the subsequent reaction without working up.

3. Preparation of

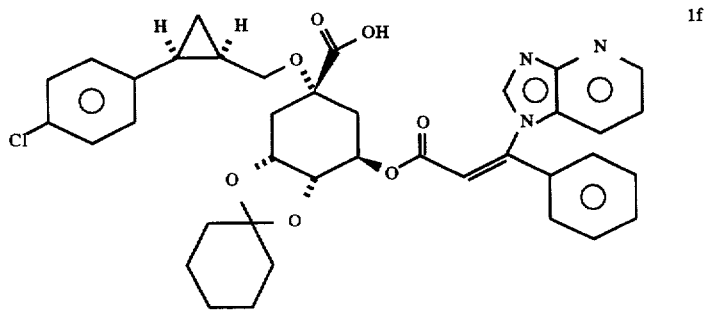

from 1e and 1F 10.1 g (23.1 mmol) of 1e are dissolved in 200 ml of anhydrous dimethylformamide and 2.08 g of 80% strength sodium hydride are added at 0°–5° C. A suspension of the sodium salt is formed, to which 1.5 eq. of the solution 1F are added dropwise at 0°–5° C. After 1 h, the reaction solution is added to 2N acetic acid. The mixture is extracted with ethyl acetate and the combined organic phases are dried using sodium sulfate. After concentrating in vacuo, the residue is purified by chromatography on silica gel (eluent ethyl acetate/n-heptane/methanol/glacial acetic acid 8:10:1:1), 5.6 g (8.19 mol) of 1f are obtained as a colorless viscous oil.

4. Preparation of the compound 1

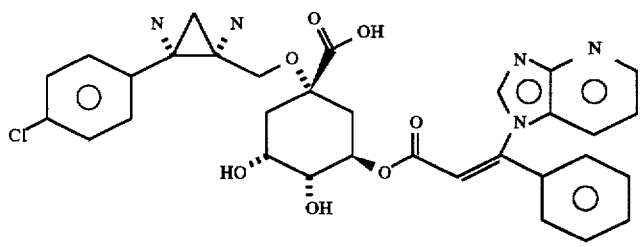

1

Preparation of 1 from 1f:

21.0 g of 1f are dissolved in 300 ml of dioxane and 75 ml of 2N HCl are added. This solution is warmed at 50°–60° C. for 2½ hours and then cooled again to 20° C. 135 ml of 1N sodium hydroxide solution are then added dropwise (pH 3). The dioxane is distilled off in vacuo and an aqueous suspension is obtained. The precipitate is filtered off with suction. 13.8 g of 1 are obtained as a colorless solid.

M.p. 158°–160° C.

The following compounds were prepared in an analogous manner.

EXAMPLE 2

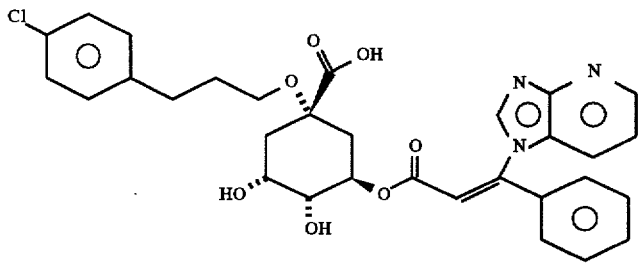

MS: m/e=592 (M+H$^+$)

EXAMPLE 3
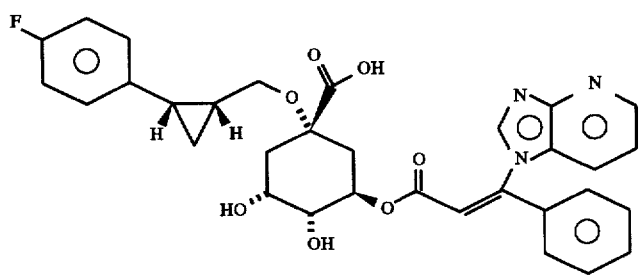
M.p.: 132°–135° C.
EXAMPLE 4
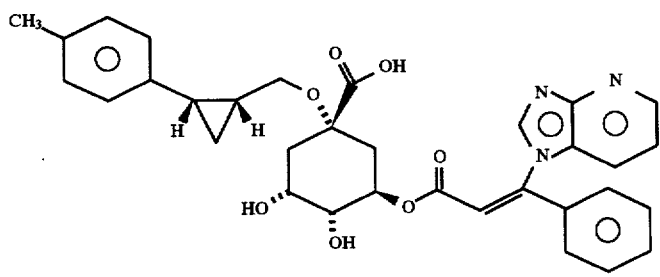
MS: m/e=583 (M+H$^+$)
EXAMPLE 5
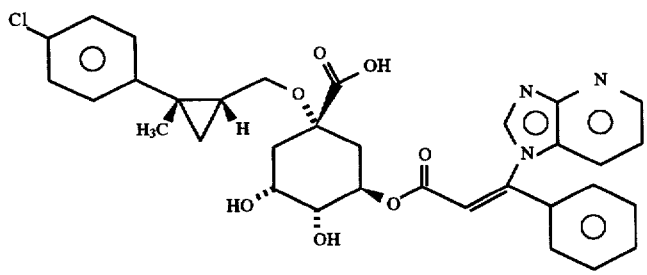
MS: m/e=618 (M+H$^+$)
EXAMPLE 6
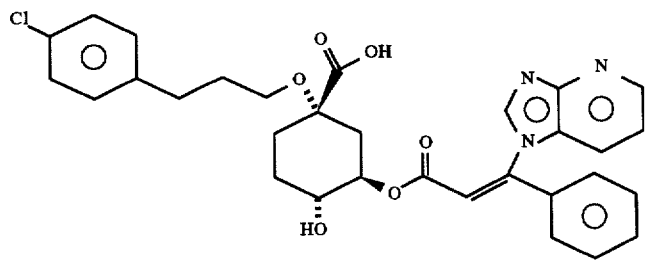
m/e=576 (M+H$^+$)

EXAMPLE 7 m/e=572 (M+H⁺)

We claim:

1. A compound of the formula wherein

R² is O—C₃-C₅-alkyl-(R¹¹), wherein alkyl is straight-chained, branched or cyclic; R¹¹ is phenyl or phenyl substituted in the 4-position by fluorine, chlorine or methyl; and R⁴ and R⁵ are identical or different and are hydrogen or hydroxyl, the physiologically tolerable salts thereof, the geometric isomers thereof, or the optical isomers thereof.

2. A compound according to claim 1 wherein alkyl is cyclic alkyl.

3. A compound according to claim 2 wherein cyclic alkyl is cyclopropyl.

4. The compound according to claim 3 wherein R² is and R⁴ and R⁵ are hydroxyl.

5. The compound according to claim 1 wherein R² is and R⁴ and R⁵ are hydroxyl.

6. The compound according to claim 3 wherein R² is and R⁴ and R⁵ are hydroxyl.

7. The compound according to claim 3 wherein R² is and R⁴ and R⁵ are hydroxyl.

8. The compound according to claim 1 wherein R² is

R⁴ is hydroxyl and R⁵ is hydrogen.

9. The compound according to claim 1 wherein R² is and R⁴ and R⁵ are hydrogen.

10. A method of treatment of diseases associated with an increased activity of the glucose-6-phosphatase system, which comprises administering to a host in need thereof an effective amount of a compound as claimed in claim 1.

11. A method of treatment of diseases associated with an increased hepatic glucose production, which comprises administering to a host in need thereof an effective amount of a compound as claimed in claim 1.

12. A method of treatment of type II diabetes (non-insulin-dependent or adult-onset diabetes), which comprises administering to host in need thereof an effective amount of a compound as claimed in claim 1.

13. A pharmaceutical composition comprising an effective type II diabetes effective amount of a compound according to claim 1 and a carrier therefor.

* * * * *

UNITED STATES PATENT AND TRADEMARK OFFICE
CERTIFICATE OF CORRECTION

PATENT NO. : 5,739,147
DATED : April 14, 1998
INVENTOR(S) : Horst HEMMERLE et al.

It is certified that error appears in the above-identified patent and that said Letters Patent is hereby corrected as shown below:

Title Page, Item [75], in the Inventors, line 4, after "Camberg", delete ";" and insert therefor --, all of Germany;--.

Title Page, Item [75], in the Inventors, line 5, delete "all of Germany" and insert therefor --Sweden--.

Signed and Sealed this

Ninth Day of March, 1999

Attest:

Q. TODD DICKINSON

*Attesting Officer*  *Acting Commissioner of Patents and Trademarks*